United States Patent [19]

Tari et al.

[11] Patent Number: 4,700,691
[45] Date of Patent: Oct. 20, 1987

[54] HEAD RESTRAINING DEVICE FOR OPERATING PROCEDURES ON THE HEAD

[75] Inventors: Gábor Tari, Csongrád; Gábor Bereczki; Ferenc Blaskovics, both of Hódmezóvásárhely, all of Hungary

[73] Assignee: Metripond Merleggyar, Hódmezóvásárhely, Hungary

[21] Appl. No.: 716,573

[22] Filed: Mar. 27, 1985

[51] Int. Cl.$^4$ ............................................. A61B 19/00
[52] U.S. Cl. ..................................... 128/1 R; 269/328
[58] Field of Search ................... 5/434, 437; 128/1 R, 128/303 B; 269/328; 297/391, 410

[56] References Cited

U.S. PATENT DOCUMENTS

| | | | |
|---|---|---|---|
| 3,957,262 | 5/1976 | McReynolds | 297/391 X |
| 4,378,108 | 3/1983 | Bailey, Jr. | 269/328 |
| 4,390,011 | 6/1983 | Evans | 128/1 R |

FOREIGN PATENT DOCUMENTS 2836646  3/1980  Fed. Rep. of Germany ...... 297/391

Primary Examiner—Stephen F. Husar
Attorney, Agent, or Firm—Handal & Morofsky

[57] ABSTRACT

The restraining and supporting device for the head of a patient comprises a head immobilizing contraption connected to the operating table, arm and hand supports for the surgeon, wherein the hand supports are fixed to the head immobilizing contraption through flexible arms, also provided with elements releasing or tightening the flexible arms, which elements are fitted to one of the fingers of the surgeon's hand, or interconnected with hand and/or foot switch. The head immobilizing contraption consists of nape support provided with a three-point bearing for the head and can be set at an adjustable height. A front support clamps down the head into the nape support and is connected to the nape support through a hinged mechanism. The flexible arms are attached to the front support of the head immobilizing contraption.

10 Claims, 2 Drawing Figures

HEAD RESTRAINING DEVICE FOR OPERATING PROCEDURES ON THE HEAD

FIELD AND BACKGROUND OF THE INVENTION

The present invention relates to an operating device provided with head restraining means connectible to an operating table, as well as with arm and hand supports, which enables the operating surgeon to perform the operation in a more efficient manner and, which can be successfully used during eye surgery, plastic surgery on the face, as well as in case of ear-nose-laryngological or nerve surgical procedures.

In the course of the development of the surgery and its associated sciences, ophthalmology has become a more and more extensively used operative procedure requiring more and more complicated and refined technique, such as microtechnique, and at the same time, it is associated with manual activities concentrated on a narrow operative field. In comparison with the other surgical areas, such operation is the most concentrated with respect to the activity and procedure involved. A single tiny movement, momentum or tremor may be determinative on the outcome of the process; the patient will be able to see, or becomes blind. The precise planning and execution of the immobility or micro-movements represent a serious task to be faced. The practice is, however, far behind. A study of the process in ophthalomological operations reveals that due to the lack of suitable clamping or immobilization, the patient is not likely capable for a steady co-operation to achieve immobility. Apart from the stress condition culminating from the situation, the incidental pain-reflex may also contribute to it, since pain-endurance in the final analysis is a matter of intelligence, therefore, particularly in the case of children, old people with declining health, an age-group where the number of ophthalmological interventions is higher, an even less reliable co-operation can be expected. (In certain types, or phases of incidental anaesthesia, the so-called "ancient" defensive reflexes may also arise through shutting out the consciousness.) Furthermore, the head of the patient is usually held by an assistant. Another factor which cannot be left out of consideration, is the hand of the operating surgeon: not every hand which is qualified for surgery is devoid of micromovements, tremors. Naturally these will become even more intensified physiologically in contrast to professional knowledge, and power of judgement which improve with age.

It can be frequently noticed during an operation, that in the critical moments the surgeon rests his hand, for example, against the forehead, nose, or breast of the patient or against the hand, etc. of his assistant. His attention is concentrated elsewhere, but performs alternative movements at the same time, so to say, requiring the subject of the present invention.

Apart from restraining the patient's head, fixing of his eyeball is also required, which is done with the so-called "stitching thread", since during operation the eye turns reflexively upwards, but this too is held by an unsupported human hand.

Thus relatively everything moves, in spite of the strict requirement for immobility.

More and more devices are available among the improving surgical aids, which are aimed at solving the above-described problems. The so-called pillory-type head support is used e.g., which is an annular extension and intends to prevent a passive or involuntary turn of the head to the side in some extent. This simple device, however, does not inhibit at all the active movement of the head, or the incidental reflex to sit up.

A similar device is describe in U.S. Pat. No. 4,019,727, which fixes the head not by an annular element only, but it also consists of a plate bent along a curve, the position of which is adjustable in relation to the base plate. The adjustment with such a device basically amounts to tipping, but the device does not allow for a complex adjustment and for a safe restraining or clamping.

A safer restraining becomes possible by the solution offered by U.S. Pat. No. 3,957,262. Here the head restraining device is a helmet-like elastic support, which can be fixed at varying height and angular positions. However, here the device functions also essentially with a two-point clamping, which as far as keeping an accurate position is not satisfactory and, it does not offer any aid for supporting the hand and arm of the surgeon performing the operation.

A safer restraining exists according to the solution described in U.S. Pat. No. 4,097,038, used in brain surgeries. Here the skull is held by a curved frame carried by a mechanism adjustable in several directions in such a fashion, that the cranial bone is fixed by a pin adjustable with a screw to a supporting element, the position of which is adjustable by a screw. The clamping is effected directly to the bone, thus it functions with a fairly rough intervention, which is unjustifiable in case of ear-nose-laryngological procedures. Apart from this, the clamping or anchorage here is based also on two-point support and, the hand of the surgeon is not supported at all.

A device described in Swiss Pat. No. 514,373 is used in nerve surgeries, which supports the head of the patient in case of procedures performed in a sitting position. In essence, the device is a U-shaped head support fitted with a complicated adjusting mechanism, which is practically useless for ophthalmological operations.

For the purpose of ophthalmological operations various semi-circular supports connectible to a table have already been produced for support of the arm onto which the surgeon rests his elbow. These, however, do not follow the two basic, but frequently changing positions of the ophthalmologist, who operates either from behind the head or from the side.

Such arm support is described, for example, in German Pat. No. 23 52 026. Here the arm supporting plates run on a circular rail, their movement is difficult and the spatial adjustment is practically not solved. Its fundamental shortcoming is that it supports the arm, not the hand, and in certain postures, or in operating positions, it inhibits rather than assists the task of the surgeon.

The most up-to-date operative microscopes attempt to meet the general demand for a support of the hand. Hinged, extendable extensions are fitted to the chair of the microscopes, which fix not only the arm but also the wrist joint as well, since in micro-surgeries, working only with finger movements is desirable. Naturally these can be used only in a sitting position, because of the frequent change in the posture.

Consequently, the hand becomes even more uncertain. Such hand supports enjoy a general acceptance in hand surgery, even that their adjustment is difficult, and dimensionally the adjustment possibility is very restricted.

SUMMARY AND OBJECTS OF THE INVENTION

An object of the present invention is to provide an operating apparatus primarily for ophthalmological operations, which ensures a perfect anchorage or clamping of the sick organ and enable a safe support of the surgeon's hand in an optional position, as well as an easy and quick change of the supporting position during operation.

The above object is achieved according to the present invention by providing an operating device with head securing or fixing means attachable to the operating table, as well as with arm and hand supports for the surgeon, the hand supports being fixed to the head restraining device with the aid of adjustable arms and, provided with elements for releasing or tightening the arms. The adjustable arms may be flexible or hinged rods which are attached to the head fixing device preferably by releasable joints. The hand supports for the surgeon are preferably triangular plates, the vertices of which are rounded. The plates are fastened to the flexible arms at one of the vertices, while they are bent-up like a flange, at the other two vertices.

The elements releasing or tightening the flexible arms may be eccentric cams with arms, the latter being fitted to one of the fingers of the hand, such as to the thumb by a ring position, where the geometric axis of the ring on the ends of the eccentric arms fitted to the thumb is parallel with the plane of the aforementioned flanges of the plate.

The elements for releasing or tightening the arms may be in the form of pneumatic cylinders, mechanical or electromechanical actuating elements. In this case they are actuated suitably with foot switch.

The head restraining means of the device is rigidly connected to the operating table in an adjustable height and comprises a nape-support assuring a three-point bearing for the head, and a front support pinning down the head to the nape support and being connected through a hinged mechanism to the nape support and wherein the adjustable arms are fixed to the front support. Further flexible arm or arms may be fixed to the front support, the ends of which may be fitted with a manipulator, such as a spring-actuated clamp, or carry and hold other instruments.

The flexible arms may consist of alternately arranged sleeves and bored through balls, where the external surface of the balls abuts on internally tapered or arcuate surfaces formed on the ends of two adjacent sleeves. A wire is passed through the sleeves and balls, one end of the which is fixed in the flexible arm, while the other end is provided with a tensioning device.

The restraining device according to the present invention eminently meets the requirements arising in ophthalmological procedures: the head of the patient is restrained considerably and reliably, and the hands of the surgeon are supported in all conceivable functional positions. Its mounting is simple, its operation easy, the adjustable arms can be released by a single hand or foot movement and, upon assuming the desired position they can be tensioned again by a single movement. The correct adjustment is checked by the space-sensation of the hand performing the adjustment. Use of the apparatus considerably increased the efficiency, and safety of the operating hand, and thus the outcome of the operation as well.

The flexible arm of the manipulator is suitable for accomplishing the steady restraining not only of the head, but also the immobility of the eyeball with the anchoring threads, and at the same time, it is suitable for gripping and holding instruments, e.g. retractors. As a result, the number of the operating personnel can be reduced.

The restraining device of the present invention conforms to the medical specifications of the operating theatre.

BRIEF DESCRIPTION OF THE DRAWING

Further details of the invention are shown, by way of example, with reference to the drawings, in which.

DESCRIPTION OF THE PREFERRED EMBODIMENT

Figure 1:
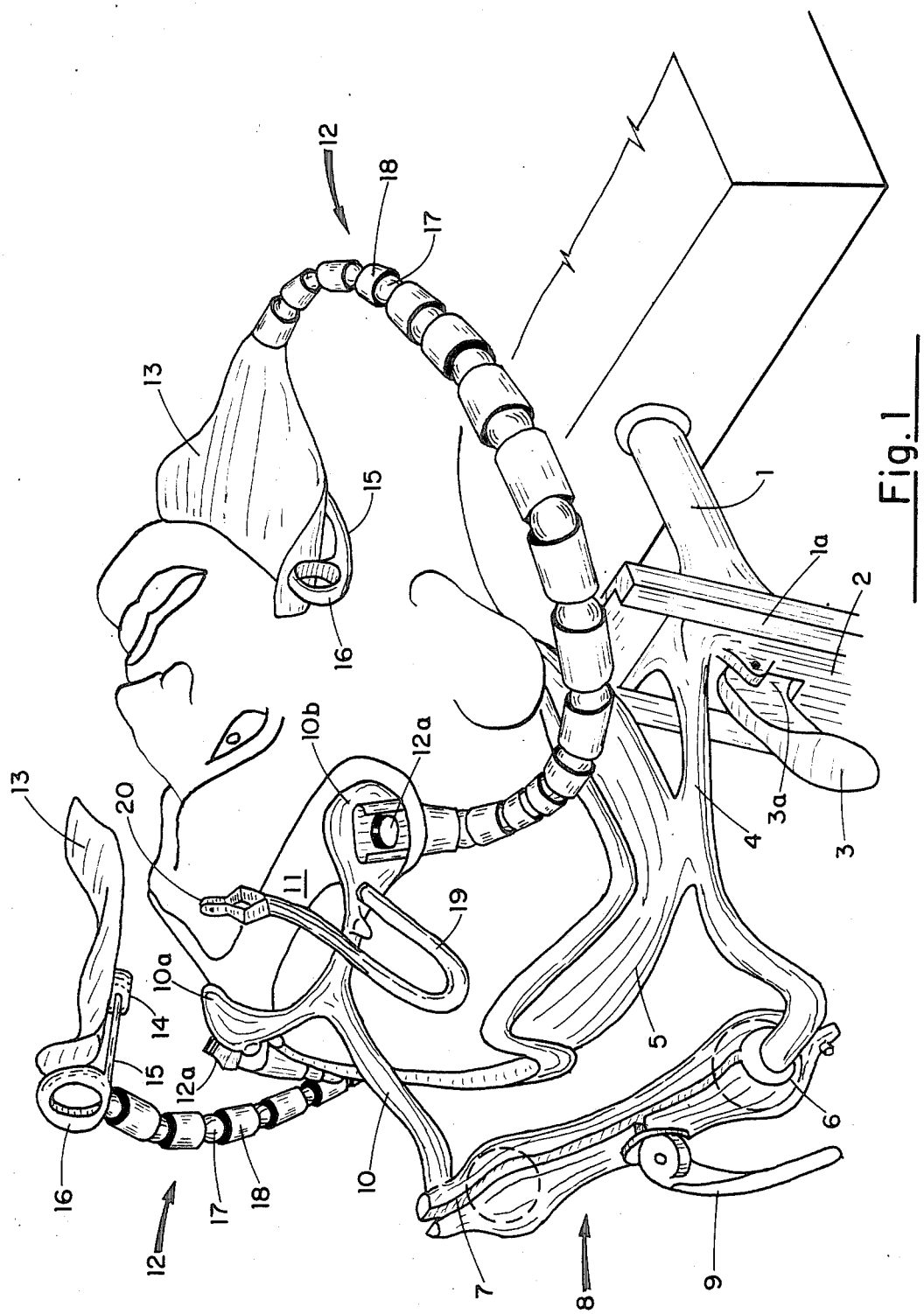
FIG. 1 shows the operating device according to the invention during an operative procedure and FIG. 2 shows the flexible arm and its coupling arrangement.

The device according to the present invention is attached to the customary operating table by a main beam 1. The connecting part of the main beam 1 is similar to the connecting part of the conventional head supports. Its other part includes a dovetail guide 1a in which a sledge 2 is moveably supported. The sledge 2 can be fixed in an appropriate position by a catch pawl 3 integral with an eccentric clamp 3a which in its clamped down position secures sledge 2.

Sledge 2 is coupled with an arm 4, a middle position of arm 4 being fixed to a nape support 5. The nape support 5 is cup-shaped having petal-like extensions, and it is symmetrically formed to conform to the cranial cavity part of the nape's occipital bone providing a further support by an extension to the adjacent frontal bone of the patient, which is known to have a flat surface compared to the whole curvature of the skull. The third extension in the axis of the symmetry extends up to a third region having a larger radius of curvature similar to the entire skull as formed at the junction of the occipital bone and the two parietal bones. Thus the nape support 5 forms three supporting surfaces in three planes. The nape support 5 is lined with thin, elastic material, such as flanged porous silicone rubber.

In some cases it may be preferred to have a formation for arm 4 and nape support 5, which enables their adjustment in relation to each other. This would be realizable in such a fashion, that the middle part of arm 4 is made heavier and provided with a vertical axial threaded hole. A threaded bar allowing for the fine adjustment and for a more reliable fixing of the nape support 5 is then fitted into such threaded hole, the upper end of which carries the nape support 5, while its lower end is provided with a turning wheel and a counter nut allowing for the fine adjustment.

A sphere 6 similar to a ball-joint is formed on the end of arm 4 for a purpose hereinafter discussed. Sphere 6 and another sphere spaced therefrom are surrounded by a ball joint clamp 8. The ball joint clamp 8 is released or tightened by a catch pawl 9. The ball joint clamp 8 with the two spheres 6 and 7 forms an adjustable coupling between arm 4 and a front part of the operating support, which is connected to the second shpere 7. The front support 10 branches off symmetrically in a Y-shape 10a and b, and is fitted on to the two frontal protruberances of the skull. Padding 11 made of elastic material is arranged below and between the two branches 10a and 10b of the front support 10, but also the apex of the Y interlinking the two branches and thereby a padded structure will embrace the forehead of the patient.

Figure 2:
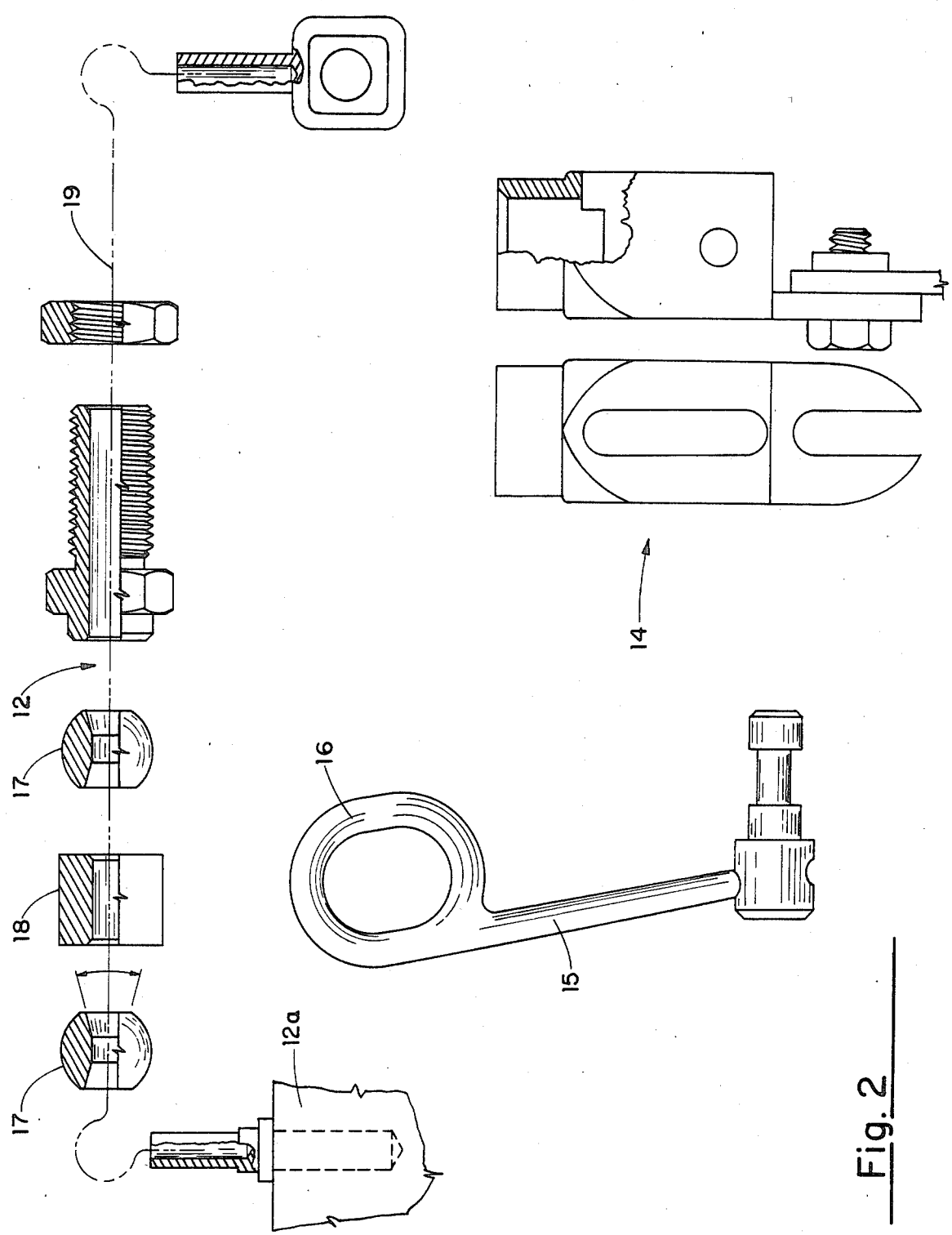

With reference to FIG. 2, it is seen that flexible arms 12 are fixed to the front support 10 at branches 10a and 10b by releasable coupling means 12a, which can be either a bolt and nut coupling or any known quick-release coupling. On the end of arms 12 hand supports 13 are adjustably arranged for the surgeon.

According to the functional requirement, the supports 13 are essentially triangular plates, the two rounded vertices of which are bent up on the side. In the axial direction the hand supports 13 are provided with convexity looking upward to the middle portion, which conforms to the negative of the mezoternar excavation between the thumb and the little finger cushion of the palm. According to the present invention, an eccentric clamp 14 for the releasing or tightening of the associated flexible arm 12 is arranged below the convexity of each support 13. Each eccentric clamp 14 is joined to an arm 15 at the end of which a ring 16 is formed. The geometric axis of each ring 16 in normal position is parallel with the longitudinal axis of the associated hand support 13. Thus the thumb of the hand of the surgeon lying on the hand support 13 fits comfortably into the ring 16, and either one of the eccentric clamps 14 can be opened or closed by movement of his finger as may be necessary during the operating procedure.

It is noted that the eccentric clamps 14 or other equivalent element for the releasing or tightening of an associated flexible arm 12 can be arranged, for example, on the end of arms 12 at the respective branches 10a or 10b of front support 10. In that case they are actuated by pneumatic cylinders, or by mechanical or electromechanical elements. These can be actuated by the surgeon with a foot switch, thus his hand is used only for the operating procedure.

The arms 12 consist of such elements which can be turned in relation to each other, and ensure the optional position of the arm. In this case the elements are balls 17 and sleeves 18, which are alternately strung on a wire. One end of the wire is fixed, preferably at the coupling points 12a while the eccentric clamp 14 is coupled to the other end of the wire in a manner that by movement of clamp 14 the length of wire is changed, therefore, it becomes loosened or tightened, which in turn implies a flexible adjustment and a secure adjusted position for the arms 12. It follows, that upon turning of the arm 15, the eccentric clamp 14 tensions or releases the wire. The friction ensures that arms 12 always remain in the set position.

Since the tautness of the wire is steplessly adjustable, the rigidity of the arms 12 is optional. By pulling on the adjusting arm 15 by force, the arm 12 becomes completely tensioned and remains in its assumed position until it is readjusted. When arm 15 is released, the arm 12 becomes loose and flexible like a wire.

Both balls 17 and sleeves 18 are provided with central holes to string them onto the wire. Apart from this, the holes of the sleeves 18 are provided with chamfer on both sides fitting in the external surface of the balls 17. This chamfer may be a simple tapered part or spherical surface conforming to the diameter of the balls 17. However, the combination of the two surfaces is also possible.

The illustrated embodiment is obviously not the only possibility for forming the arms 12. Elements different from those illustrated can also be strung onto the wire, e.g. uniform segments by the combination of balls and sleeves. An adjustable arm formed as a wind-pipe is also conceivable.

In case of larger loads, an arm formation is also conceivable, which is formed from hinged bars, and upon tightening of the hinge points, it will form an extremely rigid structure.

In addition to the adjustable arms 12 for the hand supports 13, further arms 19 may also be connected to the front support 10. Such arms 19 are provided with manipulators 20 which may be in the form of spring-actuated artery-tightening foreceps. Arms 19 may be formed similarly to the arms 12, but preferably they may be thin tubes made of soft material, such as lead alloy, which are then lined or covered in the center and outside by form-retentive, radiation-treated polyethylene wire. Though the front support as shown, has only one arm 19, it can be provided with several arms 19 for various operating procedures or instrument holders.

The disclosed embodiment demonstrates well that the device according to the invention assures the immobilization of the head and, in addition, it is provided with such hand supports, which through the front support are fixed directly to the member operated on. Thus the movement of the operated on member and of the hand in relation to each other is practically excluded. At the same time, the adjustable arms enable an optional change of the surgeon's hand position in case of necessity. A single movement of the hand or foot is required only for this purpose, and after adjustment of the new position, the flexible arms can be tightened again, thus safely holding the operating hand in the required position. The manipulators, like 19, 20, fixed to the front support 10 reduce the number of the operating personnel, thereby providing more and more space for the surgeon. At the same time the manipulator arms 19 perform certain activities more reliably, than the assistants. They are suitable for fixing the eyeball in a motionless state over an optional time, e.g. by anchoring threads, at the same time, they are suitable for gripping and holding of other instruments, such as retractors.

In case of necessity, the device according to the invention can be supplemented with such support or supports, which may be fixed directly to the operating table or to the main beam of the head support.

In this manner the device meets the requirements presented in operating procedures, since it fixed the head of the patient considerably and reliably, while the hand of the surgeon is supported safely in any conceivable position. Apart from this, the self-assisting arms 19 facilitate the execution of other activities as well.

The device is made of materials adapted in an operating theatre, such as stainless steel alloy, silicone rubber, polyethylene, lead alloy, etc., the production of which is simple and inexpensive. Its version made with reduced scale elements is suitable also for children as patients. Its use improves not only the quality of the professional human work, but also the amount of activities performed by the human hand is considerably reduced. The device of the invention conforms to the medical specifications of the operating theatre in every respect.

While the invention has been particularly shown and described with reference to a preferred embodiment thereof, it will be understood by those skilled in the art that the foregoing and other changes in form and details may be made therein without departing from the spirit and scope of the invention.

What we claim is:

1. A device for restraining and supporting the head of a patient during operating procedure, comprising head immobilizing means, means for coupling said immobilizing means to the operating table, adjustable arm means coupled to said head immobilizing means, hand support means for the operating surgeon, means for coupling said hand support means to the head immobilizing means by said adjustable arm means and including means for releasing or tightening said arm means, wherein said head immobilizing means comprises a nape support provided with a three-point bearing for the head, means for adjusting the height of said immobilizing means, a front support for clamping down the head into the nape support, a hinged mechanism connecting the front support to said nape support.

2. The head restraining and supporting device as claimed in claim 1, wherein said adjustable arm comprise alternately arranged sleeve and ball means having bores formed thereto, said sleeve means comprising internally tapered or spherical surfaces formed on both ends thereof, the external spherical surface of said ball means abutting on two adjacent sleeve means, a tensioning wire passing through said bores having one end fixed to one end of each of said adjustable arm at the front support, the other end is connected to the releasing or tightening means.

3. The head restraining and supporting device as claimed in claim 1, wherein the diameter of the adjustable arms gradually decreases from the head immobilizing means toward the other end thereof.

4. The head restraining and supporting device as claimed in claim 1, wherein the hand support means comprise triangular plates, the vertices of which are rounded and fixed to said adjustable arms by one of the vertices, while the other two vertices are bent up as a flange.

5. The head restraining and supporting device as claimed in claim 4, wherein the elements for releasing or tightening the adjustable arms are shaped to fit one end of the fingers of the hand of the surgeon.

6. The head restraining and supporting device as claimed in claim 5, wherein the releasing or tightening elements comprise eccentric clamp means comprising arm means provided with ring means fitting the thumb of the surgeon.

7. The head restraining and supporting device as claimed in claim 6, wherein the geometric axis of the ring means on the arm means of the eccentric clamp means is parallel with the plane of the flanges of the hand support means.

8. The head restraining and supporting device as claimed in claim 1, wherein at least one additional arm is fixed to the front support for holding a manipulator.

9. The head restraining and supporting device as claimed in claim 8, wherein said manipulator is a spring-actuated clamp.

10. The head restraining and supporting device as claimed in claim 8, wherein said arm is a lead-lined synthetic tube.

* * * * *